(12) United States Patent
Yao et al.

(10) Patent No.: US 7,695,751 B2
(45) Date of Patent: Apr. 13, 2010

(54) DETOXIFIZYME WITH ACTIVITY OF TRANSFORMING AFLATOXIN AND THE GENE ENCODES THEREOF

(75) Inventors: Dongsheng Yao, Guangdong (CN); Daling Liu, Guangdong (CN); Min Guan, Guangdong (CN); Chunfang Xie, Guangdong (CN)

(73) Assignee: Guangzhou Co-Win Bioengineering Co., Ltd., Guangzhou, Guangdong (CN)

( * ) Notice: Subject to any disclaimer, the term of this patent is extended or adjusted under 35 U.S.C. 154(b) by 405 days.

(21) Appl. No.: 11/629,450

(22) PCT Filed: Jan. 13, 2005

(86) PCT No.: PCT/CN2005/000050

§ 371 (c)(1),
(2), (4) Date: Dec. 13, 2006

(87) PCT Pub. No.: WO2006/017960

PCT Pub. Date: Feb. 23, 2006

(65) Prior Publication Data

US 2008/0260711 A1    Oct. 23, 2008

(30) Foreign Application Priority Data

Aug. 17, 2004  (CN) .................. 2004 1 0051120

(51) Int. Cl.
*A23J 1/00* (2006.01)
*C12N 9/00* (2006.01)
*C12N 1/20* (2006.01)
*C12N 15/00* (2006.01)
*C12P 21/06* (2006.01)
*C12P 19/34* (2006.01)
*C07H 21/04* (2006.01)

(52) U.S. Cl. .................. 426/656; 435/183; 435/193; 435/252.3; 435/320.1; 435/69.1; 435/91.1; 536/23.2; 536/23.74

(58) Field of Classification Search .................. None
See application file for complete search history.

(56) References Cited

FOREIGN PATENT DOCUMENTS

| CN | 1240828 A | 1/2000 |
|---|---|---|
| CN | 1263720 A | 8/2000 |
| CN | 1294255 C | 1/2007 |

OTHER PUBLICATIONS

Liu D L et al.: "*Armillariella tebescen* enzymatic detoxification of aflatoxin B1 (Part II)." *Annals of the New York Academy of Sciences.* Dec. 13, 1998. pp. 586-591. vol. 864.
Liu D L et al.: "Detoxification of aflatoxin B1 by enzymes isolated from *Armillariella tabescens.*" *Food and Chemical Toxicology.* Jul. 7, 1998. pp. 563-574. vol. 36.
Da ling liu et al., Production, purification, and characterization of an intracellular aflatoxin-detoxifizyme from *Armillariella tabescens* (E-20), Food and Chemical Toxicology, vol. 39, 2001, 461-466.
Da ling liu et al., "Characterization of Immobilized Aflatoxin-detoxizyme", Chinese Journal of Biotechnology, vol. 19, No. 5, 2003, 603-607.
Chitrangada Das et al., "In vitro degradation of aflatoxin $B_1$ by horse radish peroxidase", Food Chemistry, No. 68, 2000, 309-313.
R.D. Smiley et al., "Preliminary evidence that degradation of aflatoxin B1 by *Flavobacterium aurantiacum* is enzymatic", Journal of Food Protection, vol. 63, No. 3, 2000, 415-418.

*Primary Examiner*—Ganapathirama Raghu
(74) *Attorney, Agent, or Firm*—Vic Lin; Myers Andras Sherman LLP

(57) ABSTRACT

The present invention relates to a detoxifizyme with the activity of transforming aflatoxin and the gene encodes thereof. Firstly a novel protein is isolated and purified, named aflatoxin-detoxifizyme (ADTZ), which has the activity of transforming aflatoxin. The ADTZ gene is obtained through specific primers, and the gene is purified and sequenced. The gene encoding of ADTZ is cloned from the total RNA of *Armillariella tabescens*. The recombinant protein is expressed and purified through various expression systems using genetic engineering methods. The said detoxifizyme has bioactivity of transforming $AFB_1$, reducing mutagenic effects of $AFB_1$. It has great potential for the manufacturing of feed or food and development of anti-tumor medicament.

7 Claims, 3 Drawing Sheets

Figure 8:
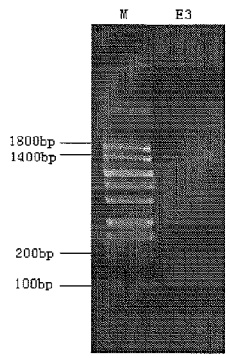

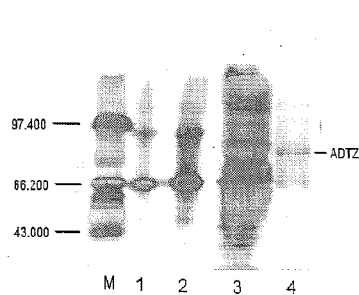
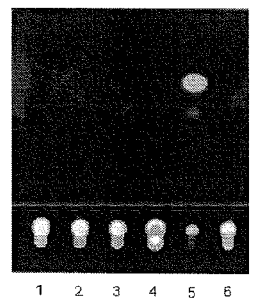
Fig. 1          Fig. 2
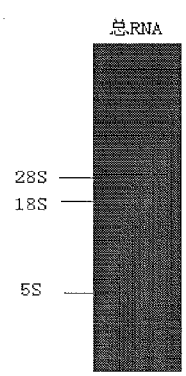
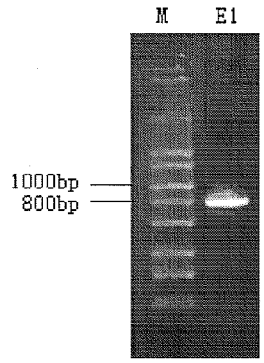
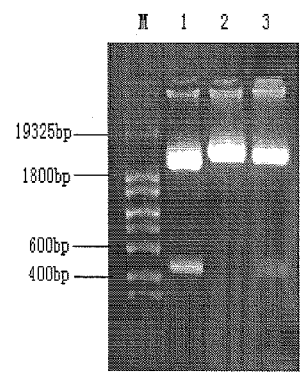
Fig. 3          Fig. 4          Fig. 5
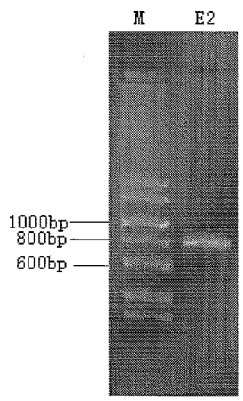
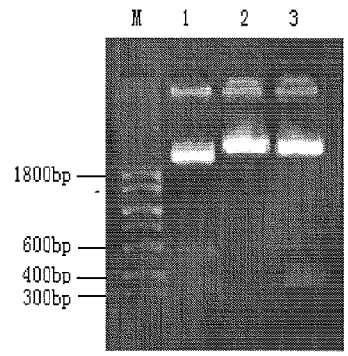
Fig. 6          Fig. 7

SEQUENCE LISTING

<160> NUMBER OF SEQ ID NOS: 2

<210> SEQ ID NO 1
<211> LENGTH: 695
<212> TYPE: PRT
<213> ORGANISM: Armillariella tabescens

<400> SEQUENCE: 1

```
Met Ala Thr Thr Thr Val His Arg Glu Arg Phe Leu Ala Asp Lys Ser
1               5                   10                  15

Ala Pro Leu Cys Gly Met Asp Ile Arg Lys Ser Phe Asp Gln Leu Ser
            20                  25                  30

Ser Lys Glu Lys Leu Tyr Thr His Tyr Val Thr Glu Ala Ser Trp Ala
        35                  40                  45

Gly Ala Arg Ile Ile Gln Ala Gln Trp Thr Pro Gln Ala Thr Asp Leu
50                  55                  60

Tyr Asp Leu Leu Ile Leu Thr Phe Ser Val Asn Gly Lys Leu Ala Asp
65                  70                  75                  80

Leu Asn Ala Leu Lys Thr Ser Ser Gly Leu Ser Glu Asp Asp Trp Glu
                85                  90                  95

Ala Leu Ile Gln Tyr Thr Val Gln Val Leu Ser Asn Leu Val Asn Tyr
            100                 105                 110

Lys Thr Phe Gly Phe Thr Lys Ile Ile Pro Arg Val Asp Ala Glu Lys
        115                 120                 125

Phe Glu Ser Val Val Lys Ala Ser Ser Asn Ala Asp Gln Gly Ser Ala
130                 135                 140

Leu Phe Thr Lys Leu Lys Gln His Ile Tyr Ala Leu Ser Pro Glu Ser
145                 150                 155                 160

Ala Leu Phe Ile Gly Lys Arg Lys Asp Gly His Val Ser Asn Tyr Tyr
                165                 170                 175

Leu Gly Glu Pro Val Gly Asp Ala Glu Val Asp Ala Ile Gln Asn Val
            180                 185                 190

Ala Glu Lys Leu Gly Val Asp Ile Leu Asn Thr Arg Val Lys Lys Asn
        195                 200                 205

Gly Ala Gly Asp Tyr Thr Leu Leu Val Ala Ser Ala Lys Thr Ser Pro
210                 215                 220

Pro Ser Val His Asp Phe Gln Ile Asp Ser Thr Pro Ala Lys Leu Thr
225                 230                 235                 240

Ile Glu Tyr Gly Asp Tyr Ala Ser Ser Leu Thr Lys Val Val Ala Ala
                245                 250                 255

Leu Gln Glu Ala Lys Gln Tyr Thr Ala Asn Asp His Gln Ser Ala Met
            260                 265                 270

Ile Glu Gly Tyr Val Lys Ser Phe Asn Ser Gly Ser Ile Pro Glu His
        275                 280                 285

Lys Ala Ala Ser Thr Glu Trp Val Lys Asp Ile Gly Pro Val Val Glu
290                 295                 300

Ser Tyr Ile Gly Phe Val Glu Thr Tyr Val Asp Pro Tyr Gly Gly Arg
305                 310                 315                 320

Ala Glu Trp Glu Gly Phe Thr Ala Ile Val Asp Lys Gln Leu Ser Ala
                325                 330                 335

Lys Tyr Glu Ala Leu Val Asn Gly Ala Pro Lys Leu Ile Lys Ser Leu
            340                 345                 350

Pro Trp Gly Thr Asp Phe Glu Val Asp Val Phe Arg Lys Pro Asp Phe
```

```
                  355                 360                 365
Thr Ala Leu Glu Val Val Ser Phe Ala Thr Gly Gly Ile Pro Ala Gly
    370                 375                 380

Ile Asn Ile Pro Asn Tyr Tyr Glu Val Arg Glu Ser Thr Gly Phe Lys
385                 390                 395                 400

Asn Val Ser Leu Ala Asn Ile Leu Ala Ala Lys Val Pro Asn Glu Glu
                405                 410                 415

Leu Thr Phe Ile His Pro Asp Asp Val Glu Leu Tyr Asn Ala Trp Asp
                420                 425                 430

Ser Arg Ala Phe Glu Leu Gln Val Ala Asn His Glu Leu Leu Gly His
                435                 440                 445

Gly Ser Gly Lys Leu Phe Gln Glu Gly Ala Asp Gly Lys Leu Asn Phe
    450                 455                 460

Asp Pro Glu Lys Val Ile Asn Pro Leu Thr Gly Lys Pro Ile Thr Ser
465                 470                 475                 480

Trp Tyr Lys Pro Gly Gln Thr Pro Asp Ser Val Leu Gly Glu Val Ser
                485                 490                 495

Ser Ser Met Glu Glu Cys Arg Ala Glu Thr Val Ala Leu Tyr Leu Val
                500                 505                 510

Ser Asn Leu Asp Ile Leu Lys Ile Phe Asn Tyr Val Asp Lys Gln Asp
                515                 520                 525

Ile Glu Asp Ile Gln Tyr Ile Thr Phe Leu Leu Met Ala Arg Ala Gly
    530                 535                 540

Leu Arg Ala Leu Glu Phe Tyr Asp Pro Ala Thr Lys Lys His Gly Gln
545                 550                 555                 560

Ala His Met Gln Ala Arg Met Gly Ile Thr Gln Tyr Leu Ile Gln Ala
                565                 570                 575

Gly Ile Ala Arg Leu Glu Leu Ile Gln Asp Ala Asn Gly Glu Leu Glu
                580                 585                 590

Asn Leu Tyr Val Arg Val Asp Arg Glu Lys Val Leu Ser Lys Gly Lys
                595                 600                 605

Glu Val Val Gly Gln Leu Leu Ile Glu Leu Gln Val Arg Lys Ser Thr
    610                 615                 620

Ala Asp Gly Thr Gly Ser Arg Asp Phe Tyr Thr Thr Leu Thr Glu Pro
625                 630                 635                 640

Ile Ser Gly Trp Glu Gly Lys Ile Arg Asp Ile Val Leu Lys Lys Lys
                645                 650                 655

Leu Pro Arg Lys Ile Phe Val Gln Pro Asn Thr Phe Val Val Asn Gly
                660                 665                 670

Glu Val Gln Leu Lys Glu Tyr Pro Leu Thr Ala Ala Gly Val Ile Glu
                675                 680                 685

Ser Phe Ile Glu Arg Arg Leu
    690                 695

<210> SEQ ID NO 2
<211> LENGTH: 2321
<212> TYPE: DNA
<213> ORGANISM: Armillariella tabescens
<220> FEATURE:
<221> NAME/KEY: CDS
<222> LOCATION: (92)...(2179)

<400> SEQUENCE: 2
acgcggggaa tcttatcctc aatcttatcg ccagccagtc acatctcttc ctttctcgag      60
aactcgtcac ctgaatacct accgcagaga a atg gcc acc aca act gtc cac cgg    115
```

```
                Met Ala Thr Thr Thr Val His Arg
                  1               5 gag cga ttc ctg gca gat aag tct gct cct ttg tgt ggt atg gat att       163
Glu Arg Phe Leu Ala Asp Lys Ser Ala Pro Leu Cys Gly Met Asp Ile
     10              15                  20 aga aag tca ttt gat cag ctc agc tct aag gaa aag ctc tac acg cat       211
Arg Lys Ser Phe Asp Gln Leu Ser Ser Lys Glu Lys Leu Tyr Thr His
 25              30                  35                  40 tac gtg acc gaa gct tct tgg gcg ggc gca aga atc atc cag gct cag       259
Tyr Val Thr Glu Ala Ser Trp Ala Gly Ala Arg Ile Ile Gln Ala Gln
                 45                  50                  55 tgg acc ccg cag gcg aca gat cta tat gat ctg ttg atc ctt acg ttc       307
Trp Thr Pro Gln Ala Thr Asp Leu Tyr Asp Leu Leu Ile Leu Thr Phe
             60                  65                  70 agc gta aat gga aag ctc gcc gac ctg aat gcc ctt aag acg tcg tca       355
Ser Val Asn Gly Lys Leu Ala Asp Leu Asn Ala Leu Lys Thr Ser Ser
         75                  80                  85 ggc ctt tca gag gac gat tgg gag gcc ttg ata cag tac acg gtc cag       403
Gly Leu Ser Glu Asp Asp Trp Glu Ala Leu Ile Gln Tyr Thr Val Gln
     90                  95                 100 gta ttg agc aat ctt gtc aac tac aag acg ttc gga ttt acg aag atc       451
Val Leu Ser Asn Leu Val Asn Tyr Lys Thr Phe Gly Phe Thr Lys Ile
105                 110                 115                 120 att ccc cgc gtc gac gca gaa aag ttt gag tca gtg gtc aaa gcc tct       499
Ile Pro Arg Val Asp Ala Glu Lys Phe Glu Ser Val Val Lys Ala Ser
                125                 130                 135 agc aac gca gac cag ggc tcg gca cta ttc acc aag ttg aaa caa cac       547
Ser Asn Ala Asp Gln Gly Ser Ala Leu Phe Thr Lys Leu Lys Gln His
            140                 145                 150 ata tat gcg ctt tct cct gag tca gcg cta ttc att ggc aaa agg aag       595
Ile Tyr Ala Leu Ser Pro Glu Ser Ala Leu Phe Ile Gly Lys Arg Lys
        155                 160                 165 gac ggt cac gta tca aat tac tat ctt ggt gaa cct gtt gga gat gct       643
Asp Gly His Val Ser Asn Tyr Tyr Leu Gly Glu Pro Val Gly Asp Ala
    170                 175                 180 gag gtc gat gct atc cag aat gtc gct gag aag tta ggc gtt gat atc       691
Glu Val Asp Ala Ile Gln Asn Val Ala Glu Lys Leu Gly Val Asp Ile
185                 190                 195                 200 ctc aat act cgc gtg aag aag aat gga gcg ggt gat cac acg ctc tta       739
Leu Asn Thr Arg Val Lys Lys Asn Gly Ala Gly Asp His Thr Leu Leu
                205                 210                 215 gtt gcc tct gct aaa acc agt cca ccc tcc gtg cat gac ttc caa atc       787
Val Ala Ser Ala Lys Thr Ser Pro Pro Ser Val His Asp Phe Gln Ile
            220                 225                 230 gac tca act ccg gct aaa ttg acg att gag tat ggc gac tac gcg tca       835
Asp Ser Thr Pro Ala Lys Leu Thr Ile Glu Tyr Gly Asp Tyr Ala Ser
        235                 240                 245 tct cta acg aag gtt gtc gcc gcc ctt cag gag gcc aaa cag tat acc       883
Ser Leu Thr Lys Val Val Ala Ala Leu Gln Glu Ala Lys Gln Tyr Thr
    250                 255                 260 gcg aac gat cat caa tca gcg atg atc gaa ggc tat gtc aag tcg ttc       931
Ala Asn Asp His Gln Ser Ala Met Ile Glu Gly Tyr Val Lys Ser Phe
265                 270                 275                 280 aac tca gga tca att ccg gaa cac aaa gct gcg tca aca gaa tgg gtg       979
Asn Ser Gly Ser Ile Pro Glu His Lys Ala Ala Ser Thr Glu Trp Val
                285                 290                 295 aaa gat att gga ccg gtt gta gag tcc tac atc ggg ttc gtc gaa acc      1027
Lys Asp Ile Gly Pro Val Val Glu Ser Tyr Ile Gly Phe Val Glu Thr
            300                 305                 310
```

```
tat gtc gac cca tat ggc gga cgc gcg gaa tgg gag ggt ttc act gcc    1075
Tyr Val Asp Pro Tyr Gly Gly Arg Ala Glu Trp Glu Gly Phe Thr Ala
        315                 320                 325 atc gtc gac aag cag ctg agt gcg aag tac gaa gca ttg gtt aac ggt    1123
Ile Val Asp Lys Gln Leu Ser Ala Lys Tyr Glu Ala Leu Val Asn Gly
330                 335                 340 gct cct aag ttg atc aag agt ctt ccg tgg gga acg gac ttc gag gtt    1171
Ala Pro Lys Leu Ile Lys Ser Leu Pro Trp Gly Thr Asp Phe Glu Val
345                 350                 355                 360 gtc gtc ttc agg aag ccg gac ttt act gcg ttg gaa gtc gta tca ttt    1219
Asp Val Phe Arg Lys Pro Asp Phe Thr Ala Leu Glu Val Val Ser Phe
                365                 370                 375 gca aca gga ggt att cct gcc gga atc aat ata cca aac tat tat gaa    1267
Ala Thr Gly Gly Ile Pro Ala Gly Ile Asn Ile Pro Asn Tyr Tyr Glu
            380                 385                 390 gtc cgg gaa agc aca ggg ttt aag aat gtt tcg cta gcg aat att ttg    1315
Val Arg Glu Ser Thr Gly Phe Lys Asn Val Ser Leu Ala Asn Ile Leu
        395                 400                 405 gcg gcc aag gca cca aac gag gag tta act ttc atc cat cct gat gac    1363
Ala Ala Lys Val Pro Asn Glu Glu Leu Thr Phe Ile His Pro Asp Asp
410                 415                 420 gta gaa cta tat aac gct tgg gat agt cgc gcg ttt gaa ctt cag gtg    1411
Val Glu Leu Tyr Asn Ala Trp Asp Ser Arg Ala Phe Glu Leu Gln Val
425                 430                 435                 440 gcc aac cac gaa ctt ttg ggt cat ggc tcc ggc aag ctt ttc caa gaa    1459
Ala Asn His Glu Leu Leu Gly His Gly Ser Gly Lys Leu Phe Gln Glu
                445                 450                 455 ggt gct gat ggg aaa ctg aac ttc gat ccc gaa aag gtc ata aac cct    1507
Gly Ala Asp Gly Lys Leu Asn Phe Asp Pro Glu Lys Val Ile Asn Pro
            460                 465                 470 ctg act gga aag ccg ata act tca tgg tat aag cca ggg caa acg ccg    1555
Leu Thr Gly Lys Pro Ile Thr Ser Trp Tyr Lys Pro Gly Gln Thr Pro
        475                 480                 485 gat tct gtt tta ggc gaa gtg tcg tcg tca atg gaa gaa tgt cgg gcg    1603
Asp Ser Val Leu Gly Glu Val Ser Ser Ser Met Glu Glu Cys Arg Ala
490                 495                 500 gag acc gta gcg ctc tac ttg gtt agc aac ctc gat att ctt aaa att    1651
Glu Thr Val Ala Leu Tyr Leu Val Ser Asn Leu Asp Ile Leu Lys Ile
505                 510                 515                 520 ttc aat tac gtc gac aag caa gac att gaa gat atc cag tac atc acg    1699
Phe Asn Tyr Val Asp Lys Gln Asp Ile Glu Asp Ile Gln Tyr Ile Thr
                525                 530                 535 ttc ttg ctt atg gcc cgc gct ggt ctg cgg gca cta gag ttt tat gat    1747
Phe Leu Leu Met Ala Arg Ala Gly Leu Arg Ala Leu Glu Phe Tyr Asp
            540                 545                 550 cca gcc acc aag aag cac gga cag gca cat atg cag gcc aga atg ggc    1795
Pro Ala Thr Lys Lys His Gly Gln Ala His Met Gln Ala Arg Met Gly
        555                 560                 565 ata acc cag tac ctg att caa gct ggg att gcg aga ctt gaa ttg atc    1843
Ile Thr Gln Tyr Leu Ile Gln Ala Gly Ile Ala Arg Leu Glu Leu Ile
570                 575                 580 cag gat gcc aac ggc gaa ctc gaa aac tta tac gtt cgg gtt gac cgg    1891
Gln Asp Ala Asn Gly Glu Leu Glu Asn Leu Tyr Val Arg Val Asp Arg
585                 590                 595                 600 gag aaa gtg ttg tcc aaa gga aag gag gtt gtt ggt caa ttg ctg atc    1939
Glu Lys Val Leu Ser Lys Gly Lys Glu Val Val Gly Gln Leu Leu Ile
                605                 610                 615 gaa ctc caa gtc cgg aaa agt acc gca gac ggc acc ggc tcc cga gat    1987
Glu Leu Gln Val Arg Lys Ser Thr Ala Asp Gly Thr Gly Ser Arg Asp
            620                 625                 630
```

-continued

```
ttc tac aca acg ctg acc gaa cca atc tct gga tgg gag ggc aag atc     2035
Phe Tyr Thr Thr Leu Thr Glu Pro Ile Ser Gly Trp Glu Gly Lys Ile
        635                 640                 645 cga gac atc gtt ttg aag aag aag ctt cct cga aaa atc ttt gtc caa     2083
Arg Asp Ile Val Leu Lys Lys Lys Leu Pro Arg Lys Ile Phe Val Gln
    650                 655                 660 ccc aat aca ttt gtc gtc aac ggc gaa gtc cag ctc aaa gag tat cct     2131
Pro Asn Thr Phe Val Val Asn Gly Glu Val Gln Leu Lys Glu Tyr Pro
665                 670                 675                 680 ttg acg gct gcc ggg gta att gaa agt ttc att gag aga cga ttg tga     2179
Leu Thr Ala Ala Gly Val Ile Glu Ser Phe Ile Glu Arg Arg Leu *
                685                 690                 695 tgtcagagcc aattgacaaa ctgaattgat gaatgatgta gtaaatgacg tgatcgtagc   2239
tgataagata agatgtattc aaataacaat tctacccaaa tatttgttca attcgaaaaa   2299
aaaaaaaaaa aaaaaaaaaa aa                                            2321
```

DETOXIFIZYME WITH ACTIVITY OF TRANSFORMING AFLATOXIN AND THE GENE ENCODES THEREOF

FIELD OF INVENTION

The present invention relates to a detoxifizyme with the activity of transforming aflatoxin and the gene encodes thereof.

BACKGROUND OF INVENTION

Aflatoxins, a group of toxic mycotoxins, including Aflatoxin B1 (AFB1), Aflatoxin M1 (AFM1), Aflatoxin G1 (G1) etc., are produced by many species of *Aspergilus*. Aflatoxins are toxic and carcinogenic to animals and humans. Aflatoxins are widely present in grain, feed, and food, and the harmful effects to human beings are: (1) direct poisoning by consumption of untreated aflatoxins contaminated food; (2) poisoning by consumption of poultry, milk, etc. indirectly from untreated aflatoxins contaminated feed; (3) waste and disposal of crops or nuts contaminated with aflatoxins.

Because of these harmful effects, detoxification of aflatoxins has been studied for years. Some methods of transforming aflatoxins already exist, for instance: (1) Ammonization method: this method is used for wet feed. Because of the large amount of residual ammonia, it is banned in food processing by FDA. The application on feed is also limited. (2) NaOH method (for vegetable oil): due to high equipment investment, oil consumption, and cost, the method is no longer in use (3) White soil adsorption method: no longer in use because of higher labor cost, pollution etc. (4) Extraction method (for peanut powder, cotton seed, etc): it isn't widely used because of the high cost associated with extracting, recovering the solvent. (5) Heat method (268° C.): cost for heating and lose of flavor and nutrients make it less practical. (6) Biological method: bacteria or immobilized bacteria are used to resolve aflatoxins. Bacteria can destroy the nutrients of food; and the products and their toxicities are not well understood. Thus this application is limited to only a few types of feed and peanut oil. (7) Ultraviolet method: strong ultraviolet oxidation used to destroy aflatoxins is not consistent and high energy consuming. (8) Ultra-filtration method: it isn't practical due to high equipment cost and rigorous technical requirement. (9) Enzyme method: clone of liver cytochrome oxidase P450 in *E. coli* was used to transform aflatoxins (Brown D W, etc. Proc. Natl. Acad. Sc. USA. 1996).

To summarize, the chemical or physical methods to transform aflatoxins often require harsh conditions, but results in lower value for the treated grain, feed, and food. These methods are often not efficient and economical, thus difficult for large scale applications. P450 enzyme method does promote the metabolism of aflatoxins, but it may also lead to higher toxicity of AFB1 to human. Because of the specificities and high efficiencies of enzymes, more research is focused on enzymes that can transform aflatoxins directly.

SUMMARY OF THE INVENTION

The present invention is generally directed to a detoxifizyme that can transform aflatoxins and gene encoding of the enzyme.

This enzyme with $AFB_1$ transforming activity can be prepared from purification of crude enzyme produced from selected cells. The $AFB_1$ transforming protein can also be produced by DNA recombinant techniques. This new active protein is named Aflatoxin-detoxifizyme (ADTZ).

The primers specific to the ADTZ gene can be obtained from purification and sequencing. The gene encoding of ADTZ can be cloned from the total RNA of *Armillariella tabescens*. The gene is a new gene that is never reported before. The recombinant protein can be expressed and purified from different expression systems, *Pichia pastoris* expression system, for example, using genetic engineering methods. The selected fungus, *Armillariella tabescens*, comes from China General Microbiological Culture Collection Center (CGMCC).

Purification of ADTZ: break the fungus cell firstly, then obtain the crude protein by $(NH4)_2SO_4$ precipitation method. ADTZ N-terminal peptide amino acid sequence can be obtained from mass spectrometry analysis of the target peak.

Purification of ADTZ: At first we and precipitates proteins by the method of ammonium sulphate precipitate method. Secondly, we receive the purpose peak from the end short peptide of the order of amino acid.

This invention relates to the extraction of total RNA of *Armillariella tabescens*. Through PCR and SMART RACE of the primers derived from the sequence of ADTZ N-terminal peptide amino acid sequence, ADTZ gene encoding can be obtained, its length is about 2.3 kb. The sequence contains a complete open reading frame, 3' and 5' non-translating regions. The ADTZ encoding cDNA contains 2088 base pairs. ADTZ mature peptide contains 695 amino acids, molecular weight: 73-77 kDa (SDS-PAGE), pI: 5.3-6.8 (isoelectric focusing electrophoresis). Amino acids and DNA sequences are depicted in the Sequence Listing (SEQ ID No.1 and SEQ ID No.2). The protein claimed in the invention should be understood to include the molecular produced by elimination, substitution, modify and addition etc.

This invention provides the recombinant expression carrier which comprises said gene, and the transformant obtained by a host cell transformed with said recombinant expression carrier. This invention further provides the method for the preparation of said detoxifizyme, which comprises: cultivating said transformant, and recovering the expressed detoxifizyme.

This invention relates to a pair of primers to amplify the gene encoding of ADTZ mature peptide from cDNA of *Armillariella tabescenes*. The DNA can be cloned to eukaryotic integration type expression vectors, such as pHIL-S1. Expression plasmid pHIL-S1-ADTZ can be thus constructed from transformation of recombinant expression vector in *Pichia pastoris* GS115. This recombinant expression vector uses AOX as promoter. Experiments on time of cultivation and induction, lead to over 25% expression of ADTZ in total protein in soluble state.

The invention relates to eukaryotic expression systems, including endocytic vectors (such as PAO815, PPIC3K, PPICZ, PHWO10, PGAPZ), or excretion vectors (such as PPIC9K, PPICZα, PGAPZα, or other commercial vectors). For eukaryotic expression stains, *Pichia pastoris* KM71, MC100-3, SMD1168, SMD1165, SMD1163 can also be used as host cells.

The invention relates to prokaryotic expression systems. Different expression vectors can be used, such as pET, pUCH33, or similar commercial vectors. For prokaryotic expression stains, *E. coli* BL21, *E. coli* JM109 can be used as host cells.

Replication of expression vectors can be achieved following Sambrook's manual (Sambrook, et al. 2002, molecular cloning, Cold Spring Laboratory Press. USA). Preparation and transformation of *E. coli* DH5α may be achieved using calcium chloride protocol. Cell culture can be prepared using ampicillin (100 μg/ml) in LB media, and plasmid extracted using alkaline method.

This invention relates to the optimal conditions to purify recombinant ADTZ. The expression culture can be first precipitated with $(NH_4)_2SO_4$. The resultant crude enzyme can be further purified by hydrophobic interaction chromatography and metal-chelating affinity chromatography to give recombinant ADTZ, which purity is greater than 95%.

The invention provides the use of said detoxifizyme with activity of transforming aflatoxin for the manufacturing of feed or food. ADTZ can be used as a detoxification additive for feed, and immobilized ADTZ can be use in detoxification of peanut oil.

The invention provides the use of said detoxifizyme with activity of transforming aflatoxin for the preparation of a medicament for preventing or treating tumor or cancer. ADTZ can be used in the prevention and treatment of aflatoxin induced tumors.

The invention relates to methods of; separation and sequencing of ADTZ gene in the first time. The gene encoding of ADTZ can be cloned by *Armillariella tabescenes* to expression vector to form recombinant transformant. The recombinant protein ADTZ can be expressed using this transformant. Recombinant ADTZ has similar activity in transforming $AFB_1$ as natural ADTZ from activity analysis. Recombinant ADTZ also significantly reduces mutagenic effects of $AFB_1$. It has great potential in feed, food and pharmaceutical industries.

BRIEF DESCRIPTION OF THE DRAWINGS

FIG. 1 shows PAGE of purified ADTZ. M: protein molecular weight standard; 1 and 2: BSA, 3: crude enzyme from ammonium sulfate precipitation. 4: purified ADTZ.

FIG. 2 shows TLC of purified ADTZ on $AFB_1$ transformation. 1: $AFB_1$ analytical standard; 2 and 3: PBS buffer solution, 4: $AFB_1$ treated with deactivated ADTZ, 5: $AFB_1$ treated with purified ADTZ, 6: $AFB_1$ analytical standard.

FIG. 3 shows electrophoresis of the total RNA of *Armillariella tabescenes.*

FIG. 4 shows electrophoresis of RT-PCR product. M: DNA marker. E1: RT-PCR product.

FIG. 5 shows enzyme incision of recombinant vector pTE1. M: DNA marker. 1: pTE1/HindIII+EcoRI, 2: pTE1/EcoRI, 3: pTE1/HindIII.

FIG. 6 shows electrophoresis of 3'RACE product. M: DNA marker. E2: 3'RACE product.

FIG. 7 shows enzyme incision of recombinant vector pTE2. M: DNA marker. 1: pTE2/HindIII+EcoRI, 2: pTE2/EcoRI, 3: pTE2/HindIII.

FIG. 8 shows electrophoresis of 5'RACE product. M: DNA marker. E3: 5'RACE product FIG. 9 shows enzyme incision of recombinant vector pTE3. M: DNA marker. 1: pTE3/HindIII+EcoRI, 2: pTE3/EcoRI, 3: pTE3/HindIII.

FIG. 10 shows electrophoresis of end to end PCR product. M: DNA marker. ADTZ': PCR product.

FIG. 11 shows enzyme incision of recombinant plasmid pSA. M: DNA marker. 1: pSA/HindIII+EcoRI, 2: pSA/EcoRI, 3: pSA/HindIII.

FIG. 12 shows SDS-PAGE of expression products. 1: negative control cell culture, 2: protein molecular weight standard, 3: BSA, 4: recombinant cell culture at 24 h, 5: recombinant cell culture at 48 h, 6: recombinant cell culture at 72 h, 7: recombinant cell culture at 96 h.

FIG. 13 shows TLC of purified recombinant ADTZ on $AFB_1$ transformation. 1: $AFB_1$ analytical standard, 2: $AFB_1$ treated with purified recombinant ADTZ, 3: $AFB_1$ treated with deactivated recombinant ADTZ, 4: buffer solution.

FIG. 14 is schematic diagram of construction of ADTZ recombinant and homogeneous recombination in *Pichia pastoris.*

DETAIL DESCRIPTION OF THE INVENTION

EXAMPLE 1

Preparation and Purification of ADTZ 1.1. Cell Culture 1.1.1 Strain: *Armillariella tabescenes.*

1.1.2 The above cells were incubated in the medium (potato liquid extraction 1 L, glucose 20 g, $KH_2PO_4$ 3.0 g, $MgSO_4.7H_2O$ 1.5 g, and trace vitamin, pH 6.6) for 25 days. First through three classes incubation: 6 days, 4 days and 4 days, then fourth class: 11 days, temperature 24-28° C. Cells were then collected.

1.2. Extraction of ADTZ

Fresh cells were frozen in liquid nitrogen, and broken into small pieces. Phosphate buffer (1:1 W/V) was added, followed by homogenation in ice bath, ultrasound sonication to smudge cells, and centrifugation at 11000-12000 g to remove precipitate. Precipitate was collected from 20-80% saturated $(NH_4)_2SO_4$ fractional precipitation and suspended in phosphate buffer (0.2 mol/L, pH 6.0). Proteins were quantitated using Bradford method, enzyme activity was tested using $AFB_1$ ELISA test kit. ADTZ enzyme solution was thus produced.

1.3. Purification of ADTZ 1.3.1. Preparation of Enzyme Sample

Enzyme sample was prepared through such steps as dialysis desalination of the crude enzyme solution in phosphate buffer (40 volumes, 0.02 mol/L, pH 6.0), and concentration by dialysis in PEG-20000 and micro membrane (0.45 μm) filtration. Proteins were quantitated using Bradford method.

1.3.2. Purification of ADTZ Enzyme by Fast Protein Liquid Chromatography (FPLC)

Columns and eluents for ion exchange chromatography and isoelectro-focusing chromatography were prepared following literature procedures (*Ion Exchange Chromatography Principles and Methods*. Pharmacia Co. Edited, Pharmacia Co., 1984, pp. 29~31; *Chromatofocusing with Polybuffer™ and PBE™,* 6th. Experimental. Pharmacia Co. Edited, Pharmacia Co., 1984, pp. 11-24). All chromatographic separations were performed on FPLC systems (Pharmacia Biotech Co., United States). Detail as following:

1.3.2.1 Anion Exchange Chromatography (1) Reagent pH 6.0, 0.2 mol/L phosphate buffer.

A: pH 6.0, 0.2 mol/L, phosphate buffer.

B: pH 6.0, 0.2 mol/L, phosphate buffer+1 N NaCl.

(2) Column Preparation

DEAE-Sephadex (50 ml) was washed with 2 volumes of phosphate buffer, and kept at room temperature for 20 min. The buffer solution was removed using a micro-pump, the process was repeated 5 times. The gel slurry was poured into a glass column (20×30 cm) and packed at a flow rate of 0.6 ml/min.

The column was washed with buffer A to equilibrate until baseline stabilized around 0. The enzyme sample was loaded onto pre-column then DEAE-Sephadex column. NaCl gradient eluting: 2 hours by buffer A, 5 hours by 0-80% buffer B and A, 2 hours by 100% buffer B, flow rate: 0.6 ml/min, inspect on UV O.D.$_{280\ nm}$. Effluents were collected using a fraction collector. After PEG-20000 dialyzed concentration, and desalination, different fractions of proteins were quantitated using Bradford method, their activities in transforming $AFB_1$ were also tested. The separation was repeated, only the active fractions were collected.

1.3.2.2. Electrofocusing Chromatography (1) Reagent

Eluent: Polybuffer™ 74 (Pharmacia Co., United States, 250 ml/bottle). 100 ml diluted to 1000 ml with water, store at 4° C.

Initial buffer solution: pH 7.4, imidazole-HCl buffer (0.025 mol/L).

(2) Column

Mono-p™ PBE 94, 5×20 cm, pre-packed column (Pharmacia Co., U.S.)

The active enzyme solution from anion exchange chromatography (6 ml, 3 mg/ml) was equilibrated using Polybuffer 74 to ~6.5 ml. Mono-p column was equilibrated with initial buffer solution for 2 hours, then changed to Polybuffer 74. Enzyme solution (2 ml) was loaded onto the column, and washed with Polybuffer 74 for 10 hours at 0.2 ml/min, inspect on UV O.D.$_{280\ nm}$. Effluents were collected using a fraction collector, 2 ml/tube (10 min/tube). Collected proteins were quantitated using Bradford method, their activities in transforming $AFB_1$ were tested.

Column was washed with 0.1 N HCl until AU ~0, and washed again with 1N NaCl, and equilibrated with initial buffer overnight. The process was repeated, and active fractions were collected.

1.3.2.3. Activity Testing Using ELISA $AFB_1$ was treated with collected protein fractions; the remaining AFB1 was measured using ELISA method. The protein fractions were heated to 100° C. for 10 min to prepare deactivated enzyme solutions as controls. The fractions that can lower the $AFB_1$ level are active fractions. Detail as following:

(1) Sample Preparation

Deactivated enzyme test mixture: $AFB_1$ (200 μl, 2.5 ng/ml in methanol)+deactivated enzyme solution (200 μl, 1.2 mg/ml).

Active enzyme test mixture: AFB1 (200 μl, 2.5 ng/ml in methanol)+active enzyme solution (200 μl, 1.2 mg/ml).

Control mixture: AFB1 (200 μl, 2.5 ng/ml in methanol)+buffer solution (200 μl).

Preparation of deactivated enzyme solutions: heated to 100° C. for 10 min.

The test mixtures were mixed thoroughly and reacted for 30 min at 30° C. After centrifugation at 3000 g for 5 min, precipitate was removed. The test mixtures were tested using ELISA test kits (AgraQuant™ Total Aflatoxin Assay 4/40, ROMER, United States). Remaining AFB1 was calculated based on a calibration curve. The different fractions from chromatographic separations were tested for their $AFB_1$ transforming activities, and the fractions that can reduce AFB1 level are active fractions. The result of remaining $AFB_1$ follows: test group with the active enzyme: 1.230±0.508 ng/ml, test group with the deactivated enzyme: 2.436±0.326 ng/ml, control group: 2.508±0.203 ng/ml.

PAGE of the active enzyme fraction showed a single band under non-reductive condition, as shown in FIG. 1.

Molecular weight of the protein is 73-76 kDa analysed by SDS PAGE. pI of the protein is 5.3-6.8 analysed by isoelectric focusing electrophoresis.

EXAMPLE 2

Activity Measurement of Purified ADTZ 2.1. Test of ADTZ Activity in Transforming $AFB_1$ To measure the activity of purified ADTZ, thin layer chromatography was used for the testing of remaining AFB1 after treatment with ADTZ. Detail follows:

2.1.1. ADTZ Enzyme Mixture $AFB_1$ solution (1 μl, 0.5 μg/μl methanol) (Alexis Biochemical's Inc., Switzerland) in a 1.5 ml centrifuge tube was evaporated under nitrogen gas. Enzyme solution (300 μl, 0.1 mg/ml), $MgSO_4$ (0.5 μl) and PEG 200 (10 μl) were added to the tube and mixed thoroughly. The mixture reacted in a water bath for 1 h at 30° C., and then added $AFB_1$ 0.5 μl per hour until the total amount of $AFB_1$ was 2 μg. After addition, the mixture reacted for another 2 h.

2.1.2. Control Mixtures

Control 1: $AFB_1$ solution 1 μl in a 1.5 ml centrifuge tube was evaporated under nitrogen gas. Deactivated enzyme solution 300 μl, deactivation at 100° C. for 5 min, $MgSO_4$ 0.5 μl and PEG 200 10 μl were added to the tube and mixed thoroughly. Control 2: $AFB_1$ solution 1 μl in a 1.5 ml centrifuge tube was evaporated under nitrogen gas. PBS buffer solution 300 μl (0.1 M, pH 6.6), $MgSO_4$ 0.5 μl and PEG 200 10 μl were added to the tube and mixed thoroughly. The two control mixtures were allowed to re-act the same manner as the enzyme mixture.

The enzyme mixture and control mixtures were extracted with 2 volumes $CHCl_3$ twice. $CHCl_3$ extract was evaporated under nitrogen gas at 45° C. The crude mixtures were re-dissolved in methanol 1 ml to get the enzyme sample and two control samples for TLC.

2.1.3. TLC Measurement

TLC plates (10×10 cm, 60 Å, Whatman, United States) were freshly activated at 100° C. for 2 h. Samples were spotted on the plates 1 cm apart, and 1 cm from the edge from left to right, 1st: $AFB_1$ (10 μl, 25 μg/ml in $CHCl_3$), 2nd, 3rd: control 2 (10 μl), 4th: control 1 (10 μl), 5th: enzyme mixture (10 μl), 6th: $AFB_1$ (10 μl, 25 μg/ml in $CHCl_3$). The plate was developed in anhydrous ether, visualized with UV light (λ 365 nm), and photographed (result as shown in FIG. 2). There is almost no shift among AFB1 standards (1st and 6th spots), deactivated enzyme mixture control (4th) and PBS buffer controls (2nd and 3rd), but significant shift for ADTZ enzyme mixture (product Rf=0.95). The product following ADTZ treatment is a lot less polar than $AFB_1$, indicating the $AFB_1$ transforming activity of purified ADTZ.

2.2. The Bioactivity of ADTZ in Transforming $AFB_1$

Microorganism reversal mutation assays (Ames assays) were conducted as following:

2.2.1. Test the Bacterial Strains

Histidine Auxotroph *Salmonella Typhimurium* strain TA98 was stored at −85° C. Genotype identification and spontaneous reversal mutation quantity determination were conducted before testing to ensure the strain meet the experiment requirement.

2.2.2. Preparation of Liver $S_9$ (a) SD rat induction: SD rats were quarantined for one week to make sure they were healthy. A polychlorinated biphenyl corn oil suspension was administered via stomach tube to rats (500 mg/kg). On the fifth day, after 12 h of starvation, the animals were decapitated.

(b) Liver $S_9$ preparation: livers were collected, weighted, and perfused in situ with ice cold sterile KCl (0.15 M), and homogenated in a homogenizer. Followed by centrifugation at 9000 g for 30 min, the supernatant was collected, tested and stored at −85° C.

2.2.3. Preparation of $S_9$ Mix

The following solutions: A, B and C were mixed with S9, and stored at 4° C. (to be used within 4 h).

A: (0.2 M, coenzyme II, sterilized by filtration) 0.2 ml.

B: (0.2 M, glucose 6-phosphate, sterilized by filtration) 0.25 ml

C: (0.4 M $MgCl_2$ 20 ml+1.65 M KCl, 20 ml+0.2 mol/L phosphate buffer, pH 7.4, 500 ml+distilled water, 313 ml, mixed and sterilized by filtration) 8.55 ml.

$S_9$: 1.00 ml.

2.2.4. Preparation of Test Mixtures

In a 30 ml test sample, conc. of ADTZ was 0.2 mg/ml, $AFB_1$ 0.2 μg/ml, pH=6.0. The mixture reacted at 28° C. for 120 min, then extracted with $CHCl_3$ in the same volume for three times. The pooled $CHCl_3$ extracts were evaporated under reduced pressure at 40° C. The extraction crude was dissolved in 6.75 ml DMSO (3.75 ml and 3 ml) as enzyme test mixture. Similarly, deactivated ADTZ (pre-treated with $CHCl_3$) was used to prepare deactivated enzyme control mixture, and buffer solution was used to prepare buffer control mixture. All these samples were kept at −15° C.

2.2.5. Reverse Mutation Assay (Ames Assay)

The test mixtures in DMSO, S9 mix and *Salmonella Typhimurium* TA98 cell culture were added to the top stratum soft agar medium, mixed thoroughly, and poured onto the minimum defined Vogel selective medium at 40° C. The plates were incubated for 72 h at 37° C., and mutant colonies in every plate were calculated.

Each sample was tested with positive control and negative control, and repeated once. The result of each sample was get from the mean value of six groups of two tests. Data were reported in number of mutant colonies, mutation rate (MR=number of mutant colonies in sample/number of mutant colonies in negative control) and inhibition ratio (={1−(number of mutant colonies in sample−number of mutant colonies in negative control)/(number of mutant colonies in $AFB_1$ control sample−number of mutant colonies in negative control)}×100%).

2.2.6. Data Evaluation Criteria

Test samples are considered Ames positive when:

a). solvent controls are in normal range;

b). test samples show positive at three different conc. (MR≧2).

2.2.7. Result

The number of mutant colonies in active enzyme test mixtures and DMSO control samples are very similar (MR<2). The number in buffer controls and deactivated enzyme test mixtures are considerably higher than DMSO control samples. In fact, they are very close to the numbers in positive controls ($AFB_1$ controls) (MR>2). The data indicates the activity of ADTZ in inhibiting mutation caused by $AFB_1$. Data are shown in the following table.

| Mutation assays of $AFB_1$ treated with ADTZ enzymes | | | |
|---|---|---|---|
| Test sample | The number of mutant colonies/plate | MR | Inhibition rate (%) |
| PBS-control | 378 ± 77 | 13.09 | ~ |
| Deactivated enzyme | 359 ± 59 | 12.86 | ~ |
| Enzyme | 31 ± 12 | 1.11 | 99.16 |
| $AFB_1$ control | 385 ± 97 | 13.75 | ~ |
| DMSO control | 28 ± 5 | ~ | ~ |

Description: mutation assays used rat liver $S_9$ and *Salmonella* Typhimurium TA 98 test strain. $AFB_1$ positive control: 0.8 μg/50 μl DMSO/plate. Enzyme test mixtures used the same amount of $AFB_1$ and DMSO. Plates were incubated for 28 h, numbers of mutant colonies were calculated. The data shown are from avenging of 4 plates±SD.

EXAMPLE 3

Sequencing of ADTZ Peptide

Samples: active fraction collected from example 1 or active fraction further purified by PAGE. ADTZ N-terminal peptide sequencing was conducted on a Micromass Q-TOF II mass spectrometer. The sequences are as following: M1: EAWEGFTALVDK M2: NKLLQDANGELENLYVR The invention relates to other peptide sequences other than the one listed above, as long as they are detected from MALDI-MS-TOF or other chemical methods on ADTZ peptide.

EXAMPLE 4

Extraction of the Total RNA of *Armillariella tabescenes*

The bacterial culture of *Armillariella tabescenes* was placed in a Petri dish on ice. The tissues was then frozen by immersion in liquid nitrogen, and grounded to powder. The powder (100 mg) was transferred into a 1.5 ml centrifuge tube and added Trizol (1 ml). The mixture was shook vigorously and incubated for 5 min at room temperature. Chloroform (200 μl) was added, the mixture was shook vigorously for 2 min, and placed in an ice bath for 5 min. The homogenate was centrifuged at 12000 g for 15 min at 2-8° C. The supernatant containing RNA was carefully transferred to another 1.5 ml centrifuge tube. Cooled isopropanol (500 μl) was added, and the mixture was placed in an ice bath for 20 min. The mixture was centrifuged at 12000 g for 10 min at 2-8° C., then supernatant was removed and the RNA pellet was washed with 75% ethanol (1 ml). The sample was centrifuged at 7500 g for 5 min at 2-8° C. Ethanol was removed and the RNA was dried for 5-10 min at room temperature.

The RNA was completely dissolved in DEPC sterile water (50 μl), and was tested by UV and electrophoresis (1.1% Agarose gel/EB 100V, 20 min) analyses before stored at −80° C. The result was shown in FIG. 3. From electrophoresis, 28 s rRNA and 18 s sRNA were clearly visible. The ratio was about 2:1. It indicates that the total RNA was not degraded.

EXAMPLE 5

Design of ADTZ Gene Primers

The invention relates to two pairs of primers (P1, P2, and G1, G2) designed according to ADTZ peptide sequence. Partial ADTZ gene sequence products were obtained from RT-PCR using QIAGEN OneStep RT-PCR kit. The RT-PCR products were TA cloned. The recombinant plasmid form TA clone was identified by HindIII and EcoRI enzyme incisions followed by electrophoresis (1.5% Agarose gel). ADTZ gene partial cDNA E1 was obtained from sequencing of the recombinant plasmid. Detail follows:

```
Primer pair 1
P1:
5'-TGGGARGGNTTYACNGC-3'

P1:
5'-TCNCCRTTNGCRTCYTG-3'

Primer pair 2
G1:
5'-CARGAYGCNAAYGGNGA-3'

G2:
5'-GCNGTRAANCCYTCCCA-3'
```

The invention relates to ADTZ specific primer pairs that are not limited to the above pairs, but also any other designed from ADTZ peptide sequence.

5.1. RT-PCR 5.1.1. Template total RNA (from Example 4) was denatured at 75° C. for 5 min, then cooled in ice bath.

5.1.2. Master Mix Preparation (80 μl System)

| |
|---|
| 42 μl RNase-free Water |
| 16 μl 5 × QIAGEN One-Step RT-PCR Buffer |
| 3.2 μl dNTP Mix (10 mM) |
| 3.2 μl OLAGEN One-Step RT-PCR Enzyme Mix |
| 64.4 μl |

Mixed thoroughly by pipetting the master mix up and down a few times.

5.1.3. Components Added in the Listed Order to a Sterile Centrifuge Tube (Unit: μl)

| Component | 1 (sample1) | 2 (−control) | 3 (sample2) | 4 (−control) |
|---|---|---|---|---|
| RNA | 1.3 | — | — | — |
| Primer P1 | 1.3 | 1.3 | — | — |
| Primer P2 | 1.3 | 1.3 | — | — |
| Primer G1 | — | — | 1.3 | 1.3 |
| Primer G2 | — | — | 1.3 | 1.3 |
| Water | — | 1.3 | — | 1.3 |
| Master Mix | 16.1 | 16.1 | 16.1 | 16.1 |
| Total Volume | 20 | 20 | 20 | 20 |

5.1.4. PCR Cycles

Reverse transcription: 50° C., 30 min
Initial PCR activation step: 50° C., 15 min
3-step cycling
15 cycles: 94° C., 40 sec
  65° C. 1 min (−1° C./cycle)
  72° C. 1 min
25 cycles: 94° C. 40 sec
  50° C. 1 min
  72° C. 1 min
Final extension: 70° C. 10 min 5.1.5. After the PCR cycles, 5 μl sample was taken for electrophoresis.

5.2. Extraction of RT-PCR Product 5.2.1. TAE electrophoretic buffer solution, and 0.8% agarose gel were prepared.

5.2.2. 50 μl RT-PCR product and 10× loading buffer were mixed and loaded.

5.2.3. Electrophoresis at 100V for 20 min.

5.2.4. Bands were observed with UV light after electrophoresis. Interesting bands were extracted from gel and transferred to a 1.5 ml sterile centrifuge tube.

5.2.5. 800 μl Buffer NT1 was added.

5.2.6. Swirled the NucleoTrap suspension vigorously to a homogeneous mixture. 10 μl was added to the centrifuge tube.

5.2.7. The centrifuge tube was immersed in water bath at 50° C. for 6 min, vortexed every two min.

5.2.8. Centrifuging at 10000 g for 30 sec at room temperature, supernatant was removed.

5.2.9. 500 μl Buffer NT2 was added, and the mixture vortexed. Centrifugation at 10000 g for 30 sec at room temperature, supernatant was removed. The process was repeated once.

5.2.10. 500 μl Buffer NT3 was added, and the mixture vortexed. Centrifugation at 10000 g for 30 s at room temperature, supernatant was removed. The process was repeated once.

5.2.11. Centrifuging at 10000 g for 30 sec, supernatant was removed. The residue was air dried for 10-25 min.

5.2.12. The precipitate was suspended in 30 μl ITE buffer (pH 8.0). This fragment was named E1. Electrophoresis of this RT-PCR product was shown in FIG. 4. A new band named E1 was observed from reaction of primer pair P1 and P2 (~800 bp).

5.3. TA Clones and Sequencing 5.3.1. Ligation by DNA ligase

The following components were added to a 1.5 m sterile centrifuge tube
  1 μl pUCm-T carrier
  3 μl E1 fragment(RT-PCR product)
  1 μl 10×buffer
  1 μl T4 DNA ligase
  4 μl sterile water, total volume 10 μl Mixed thoroughly by pipetting up and down a few times, incubated in water bath at 22° C. for at least 4 h.

5.3.2. Preparation of *E. coli* DH5α Competent Cells Using CaCl$_2$ Method

DH5α monoclone was incubated in 2 ml LB medium, shook at 37° C. overnight. 50 μl of the colony was transferred to 5 ml LB medium, shook at 37° C. for 1.5-2 h. The culture was then cooled to 0° C. by keeping the tube on ice for 30 min. The culture was transferred to a sterile centrifuge tube, and centrifuged at 5000 rpm for 5 min. Medium was decanted from the cell pellet. The pellet was re-suspended in 1.5 ml ice-cold CaCl$_2$ solution, and the tube was kept on ice for 10 min. The cells were recovered by centrifugation at 5000 rpm for 5 min, and medium was decanted. The pellet was re-suspended in 200 μl ice-cold CaCl$_2$ solution and kept at 4° C.

5.3.3. Transformation of DH5α Competent Cells

200 μl of the suspension of competent cells was transferred to a centrifuge tube containing linker DNA (10 μl). The contents were mixed by swirling gently and stored on ice for 30 min. After 90 sec in a water bath at 42° C., the contents were stored on ice for 3-5 min. Added LB medium (800 μl) and the mixture was incubated at 37° C. for 40-60 min.

The transformed competent cells were spread onto agar medium containing Amp and IPTG/X-gal (200 μl/90-mm plate) and incubated at 37° C. for 12-16 h.

5.3.4. Alkaline Extraction of Plasmid DNA

The transformed competent cells were transferred to 2 ml LB medium containing ampicillin. The culture was shook vigorously at 37° C. overnight.

The culture (1.5 ml) was transferred to micro-centrifuge tube, and centrifuged at 12000 rpm for 2 min. The supernatant was removed.

The pellet was washed with 400 μl STE solution. The contents were mixed by swirling vigorously, and centrifuged at 12000 rpm. The supernatant was removed.

The pellet was added cooled solution I, and shook vigorously, then added fresh prepared solution II, mixed well and stored on ice for 3 min.

Cooled solution III was added, mixed well, and stored on ice for 5 min.

The mixture was centrifuged at 12000 rpm for 5 min, and the supernatant was transferred to another tube.

Equal volume of phenol chloroform was added to the supernatant.

The mixture was centrifuged again. The supernatant was transferred to a third tube.

Cooled anhydrous ethanol (2 volume) was added to the third tube. After mixing, the tube was kept at room temperature for 40-60 min.

The content was centrifuged at 12000 rpm for 10 min. Supernatant was removed.

The pellet was washed with 70% ethanol (200 μl). The mixture was centrifuged again at 12000 rpm for 1 min. Supernatant was removed.

The pellet was air-dried for 5-10 min, then suspended in DNase-free RNase TE buffer, incubated at 30° C. for 1 h and stored at −20° C.

5.3.5. Identification of Recombinant Plasmid pTE1 by Enzymatic Incisions HindIII and EcoRI Enzymatic Incisions of TA Clones (Unit: μl)

| Number | Buffer M | Buffer H | HindⅢ | EcoRI | pTE1 | H₂O |
|---|---|---|---|---|---|---|
| 1 (20 μl system) | 2 | — | 1 | 1 | 10 | 6 |
| 2 (20 μl system) | — | 2 | — | 1 | 10 | 6 |
| 3 (20 μl system) | 2 | — | 1 | — | 10 | 6 |

After enzymatic incision reaction at 37° C. for 4 h, the mixtures were analyzed by 1.5% agarose electrophoresis. Results of enzymatic incision of recombinant vector pTE1 were shown in FIG. 5. HindIII+EcoRI two enzyme incision (sample 1) and HindIII single enzyme incision (sample 3) all showed the same band at 400 bp, with higher intensity for sample 1. EcoRI single enzyme incision (sample 2) showed linear cleavage. These results indicate that there is a HindIII cleavage site in E1 fragment.

5.3.6. Recombinant Plasmid DNA Sequencing

Recombinant plasmid DNA was purified by precipitation with PEG (Sambrook, et al. 1989, Molecular Cloning, Cold Spring Harbor Laboratory Press, United States). The DNA sequence of E1 fragment was determined on an ABI377 DNA sequencer using T7 and SP6 sequencing primers. The determined sequence contains P1, P2, and a HindIII cleavage site (aagctt).

EXAMPLE 6

Total cDNA Sequence of ADTZ Gene

Primers were designed from ADTZ gene fragment E1 as determined from example 5:

```
S1:
5'-TAGGCGAAGTGTCGTCGTCAATGGAA-3'

S3:
5'-GAAGTTATCGGCTTTCCAGTCAGAGGGT-3'
```

Using S1 and S3 as primers, 3'RACE and 5'RACE were conducted using SMART™ RACE cDNA amplification Kit (COLONTECH Laboratories, Inc. Cat. No. K1811-2). RACE products were recovered from scraping from gel, and TA cloned using routine method. Recombinant plasmid DNA fragments were sequenced following HindIII and EcoRI enzyme incision and analysed by 1.5% agarose electrophoresis. Fragments E2 and E3 were thus obtained. Vector sequences were removed using Vecscreen software. E1, E2 and E3 were assembled using DNAMAN software (Lynnon BioSoft). The complete cDNA sequence of ADTZ gene was obtained from open reading frame analysis using ORF Finder (NCBI). Detail follows:

```
Primer S1:
5'-TAGGCGAAGTGTCGTCGTCAATGGAA-3' primer S3:
5'-GAAGTTATCGGCTTTCCAGTCAGAGGGT-3'
```

6.1. 3'RACE 6.1.1. Preparation of 3'RACE-Ready cDNA 6.1.1.1. Template total RNA (from Example 4) was denatured at 75° C. for 5 min, then cooled in ice bath.

6.1.1.2. The following reagents were added to a 0.5 ml sterile centrifuge tube: 1 μl denatured template total RNA, 1 μl 3'-CDS primer A, and 3 μl RNase free sterile water to make the total volume 5 μl.

6.1.1.3. Mixed thoroughly by pipetting up and down a few times, followed a short centrifugation step.

6.1.1.4. Incubation at 70° C. for 2 min.

6.1.1.5. Sample was stored on ice for 2 min. After a short centrifugation step, the following reagents were added:

---
2 μl 5 × First-Strand Buffer
1 μl DTT (20 mM)
1 μl dNTP Mix (10 mM)
1 μl PowerScript Reverse Transcriptase 10 μl total volume

---

6.1.1.6. Mixed thoroughly by pipetting up and down a few times, followed a short centrifugation step.

6.1.1.7. Incubation at 42° C. for 1.5 h.

6.1.1.8. Dilution with 100 μl Tricine-EDTA.

6.1.1.9. Incubation at 72° C. for 7 min.

6.1.1.10. Storage at −20° C.

6.1.2. 3' RACE PCR 6.1.2.1. Preparation of Master Mix (100 μl System)

| | |
|---|---|
| 69 μl PCR-Grade Water | |
| 10 μl 10 × Advantage 2 PCR Buffer | |
| 2 μl dNTP Mix (10 mM) | |
| 2 μl 50 × Advantage 2 Polymerase Mix | |
| 83 μl | |

The contents were mixed thoroughly by pipetting up and down a few times, followed a short centrifugation step.

6.1.2.2. Components Added to a 0.5 ml Sterile Centrifuge Tube in the Order Listed (Unit: μl)

| Component | 1 (sample) | 2 (−control) | 3 (−control) |
|---|---|---|---|
| 3'-RACE-Ready cDNA | 2.5 | 1.5 | 1 |
| UPM (10×) | 5 | 3 | — |
| Primer S1 (10 μm) | 1 | — | 0.4 |
| H$_2$O | — | 0.6 | 2 |
| Master mix | 41.5 | 24.9 | 16.6 |
| Total volume | 50 | 30 | 20 |

6.1.2.3. PCR Cycles:

| | | |
|---|---|---|
| 5 cycles: | 94° C. | 5 sec |
| | 72° C. | 3 min |
| 5 cycles: | 94° C. | 5 sec |
| | 70° C. | 10 sec |
| | 72° C. | 3 min |
| 35 cycles: | 94° C. | 5 sec |
| | 68° C. | 10 sec |
| | 72° C. | 3 min |

6.1.2.4. After PCR cycles, 5 μl sample was used for electrophoresis, the result was shown in FIG. 6. A single band was obtained from 3'RACE (~800 bp), and named E2.

6.1.3. TA clone of RACE product, preparation of *E. coli* DH5α competent cells (CaCl$_2$ method) and alkaline extraction of plasmid DNA were conducted as described in example 5.

6.1.4. Identification of Recombinant Plasmid pTE2 by Enzymatic Incisions HindIII and EcoRI Enzymatic Incisions of TA Clones (Unit: μl)

| Number | Buffer M | Buffer H | HindIII | EcoRI | pTE2 | H$_2$O |
|---|---|---|---|---|---|---|
| 1 (20 μl system) | 2 | — | 1 | 1 | 10 | 6 |
| 2 (20 μl system) | — | 2 | — | 1 | 10 | 6 |
| 3 (20 μl system) | 2 | — | 1 | — | 10 | 6 |

After enzymatic reactions at 37° C. for 4 h, the mixtures were analyzed by 1.5% agarose electrophoresis, results as shown in FIG. 7. HindIII+EcoRI two enzyme incision (sample 1) showed two bands at 600 bp and 300-400 bp while HindIII (sample 3) single enzyme incision showed only one band at 300-400 bp, EcoRI (sample 2) showed linear cleavage. These results indicated that there is a HindIII cleavage site in E2 fragment, which is close to one end of the fragment.

6.1.5. Sequencing

Recombinant plasmid DNA was purified by precipitation with PEG (Sambrook, et al. 1989, Molecular Cloning, Cold Spring Harbor Laboratory Press, lo United States). The DNA sequence of E2 fragment was determined on a ABI377 DNA sequencer using T7 and SP6 sequencing primers. The E2 sequence contains a HindIII cleavage site (aagctt) close to 3'.

6.2. 5' RACE 6.2.1. Preparation of 5'RACE-Ready cDNA 6.2.1.1. Template total RNA was denatured at 75° C. for 5 min, then cooled in ice bath.

6.2.1.2. The following reagents were added to a 0.5 ml sterile centrifuge tube: 1 μl denatured template total RNA, 1 μl 5'-CDS primer A, 1 μl SMART II A Oligonucleotide, and 2 μl RNase free sterile water to make the total volume 5 μl.

6.2.1.3. Mixed thoroughly by pipetting up and down a few times, followed a short centrifugation step.

6.2.1.4. Incubation at 70° C. for 2 min.

6.2.1.5. Sample was stored on ice for 2 min. After a short centrifugation step, the following reagents were added:

| | |
|---|---|
| 2 μl 5 × First-Strand Buffer | |
| 1 μl DTT (20 mM) | |
| 1 μl dNTP Mix (10 mM) | |
| 1 μl PowerScript Reverse Transcriptase | |
| 10 μl total volume | |

6.2.1.6. Mixed thoroughly by pipetting up and down a few times, and a short centrifugation step.

6.2.1.7. Incubation at 42° C. for 1.5 h.

6.2.1.8. Dilution with 100 μl Tricine-EDTA.

6.2.1.9. Incubation at 72° C. for 7 min.

6.2.1.10. Storage at −20° C.

6.2.2. 5' RACE PCR 6.2.2.1. Preparation of Master Mix (110 μl System)

| | |
|---|---|
| 75.9 μl PCR-Grade Water | |
| 11 μl 10 × Advantage 2 PCR Buffer | |
| 2.2 μl dNTP Mix (10 mM) | |
| 2.2 μl 50 × Advantage 2 Polymerase Mix | |
| 91.3 μl | |

The contents were mixed thoroughly by pipetting up and down for a few times, followed a short centrifugation step.

6.2.2.2. Components added in the listed order to a 0.5 ml sterile centrifuge tube (unit: μl)

| Component | 1 (sample) | 2 (+control) | 3 (−control) | 4 (−control) |
|---|---|---|---|---|
| 5'-RACE-Ready cDNA | 2.5 | 1 | 1 | 1 |
| UPM (10×) | 5 | — | 2 | — |
| Primer S1 (10 μm) | — | 0.4 | — | — |
| Primer S3 (10 μm) | 1 | 0.4 | — | 0.4 |
| H$_2$O | — | 1.6 | 0.4 | 2 |
| Master mix | 41.5 | 16.6 | 16.6 | 16.6 |
| Total volume | 50 | 20 | 20 | 20 |

6.2.2.3. PCR cycles:

| | | |
|---|---|---|
| | 94° C. | 1 min |
| 5 cycles: | 94° C. | 30 sec |
| | 72° C. | 4 min |
| 5 cycles: | 94° C. | 30 sec |
| | 70° C. | 4 min |
| 25 cycles: | 94° C. | 30 sec |
| | 68° C. | 4 min |
| | 72° C. | 10 min |

6.2.2.4. After PCR cycles, 5 μl sample was used for electrophoresis. The result was shown in FIG. 8. A single band was obtained form 5'RACE (~1400-1800 bp), and named E3.

6.2.3. TA clone of 5' RACE product, preparation of *E. coli* DH5α competent cells ($CaCl_2$ method) and alkaline extraction of plasmid DNA were conducted as described in example 5.

6.2.4. Identification of Recombinant Plasmid pTE3 by Enzymatic Incisions HindIII and EcoRI Enzymatic Incisions of TA Clones (Unit: μl)

| Number | Buffer M | Buffer H | HindIII | EcoRI | pTE3 | $H_2O$ |
|---|---|---|---|---|---|---|
| 1 (20 μl system) | 2 | — | 1 | 1 | 10 | 6 |
| 2 (20 μl system) | — | 2 | — | 1 | 10 | 6 |
| 3 (20 μl system) | 2 | — | 1 | — | 10 | 6 |

Figure 9:
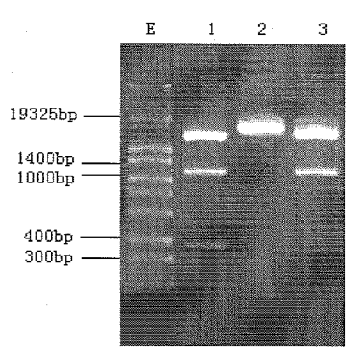

After enzymatic reactions at 37° C. for 4 h, the mixtures were analyzed by 1.5% agarose electrophoresis, results as shown in FIG. 9. HindIII+EcoRI two-enzyme incision (sample 1) showed two bands at 1400-1000 bp and 300-400 bp while HindIII (sample 3) single-enzyme incision showed only one band at 1400-1000 bp. These results indicated existence of a HindIII cleavage sites in E3 fragment.

6.2.5. Sequencing

Recombinant plasmid DNA was purified by precipitation with PEG (Sambrook, et al. 1989, Molecular Cloning, Cold Spring Harbor Laboratory Press, United States). The DNA sequence of E3 fragment was determined on an ABI377 DNA sequencer using T7 and SP6 sequencing primers. The E3 sequence contains two HindIII cleavage sites, one close to 3'and the other close to 5'.

6.3. Assembly of ADTZ cDNA Sequence Fragments

Vector sequences were removed using Vecscreen software. E1, E2 and E3 were assembled using DNAMAN software. The complete cDNA sequence of ADTZ gene was obtained from open reading frame analysis using ORF Finder (NCBI), which contains complete open reading frame with 3' poly(A) tail, 5' and 3' non-translating regions. The results were shown in the Sequence Listing as SEQ ID No.2.

BLAST and BLASTX were used for sequence similarity search on ADTZ cDNA sequence and calculated protein sequence. The search identified ADTZ cDNA as a new sequence. ADTZ mature peptide sequence calculated from ADTZ cDNA was identified as a new peptide from search in GENEBANK.

The invention relates to not only the method described in this example, but also clone of this sequence in *Armillariella tabescens* cDNA data bank using probe designed from ADTZ peptide sequence.

EXAMPLE 7

Synthesis of ADTZ Mature Peptide Gene Encoding cDNA

According to 3' and 5' end cDNA sequences, a pair of primes was designed to obtain open reading frame sequence.

P3:

5'-GTC<u>GAATTC</u>ATGGCCACCACAACTGTC-3'

P4:

3'-GTAACTCTCTGCTAACACT<u>CCTAGGGAC</u>-5'

Enzyme cleavage sites EcoR1 (GAATTC) and BamHI (GGATCC) were incorporated to the primers. PCR amplification was performed and PCR product was scraped off from the agar. Detail follows:

7.1. Preparation of Master Mix (100 μl System)

| |
|---|
| 69 μl PCR-Grade Water |
| 10 μl 10 × Advantage 2 PCR Buffer |
| 2 μl dNTP Mix (10 mM) |
| 2 μl 50 × Advantage 2 Polymerase Mix |
| 83 μl |

The contents were mixed thoroughly by pipetting up and down for a few times, followed a short centrifugation step.

7.2. Components Added in the Listed Order to a 0.5 ml Sterile Centrifuge Tube (Unit: μl)

| Component | 1 (sample) | 2 (−control) | 3 (−control) |
|---|---|---|---|
| 5'-RACE-Ready cDNA | 2.5 | — | 1 |
| Primer P3 (10 μm) | 1 | 0.6 | — |
| Primer P4 (10 μm) | 1 | 0.6 | — |
| $H_2O$ | 4 | 3.9 | 2.4 |
| Master mix | 41.5 | 24.9 | 16.6 |
| Total volume | 50 | 30 | 20 |

7.3. PCR Cycles.

| | | |
|---|---|---|
| | 94° C. | 1 min |
| 5 cycles: | 94° C. | 30 sec |
| | 72° C. | 4 min |
| 5 cycles: | 94° C. | 30 sec |
| | 72° C. | 4 min |
| 35 cycles: | 94° C. | 30 sec |
| | 68° C. | 4 min |
| | 72° C. | 10 min |

Figure 10:
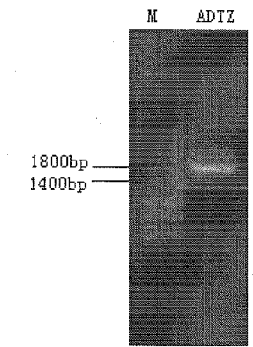

7.4. After PCR cycles, 5 μl sample used for electrophoresis, the result was shown in FIG. 10. A single band obtained from PCR (~1800 bp) was named ADTZ' fragment.

5. Recovery of PCR Product

PCR product was scraped off from the gel. The cDNA encoding ADTZ mature peptide was thus obtained. This fragment was named "ADTZ'"

EXAMPLE 8

Construction of Recombinant ADTZ Expression Plasmid

Figure 14:
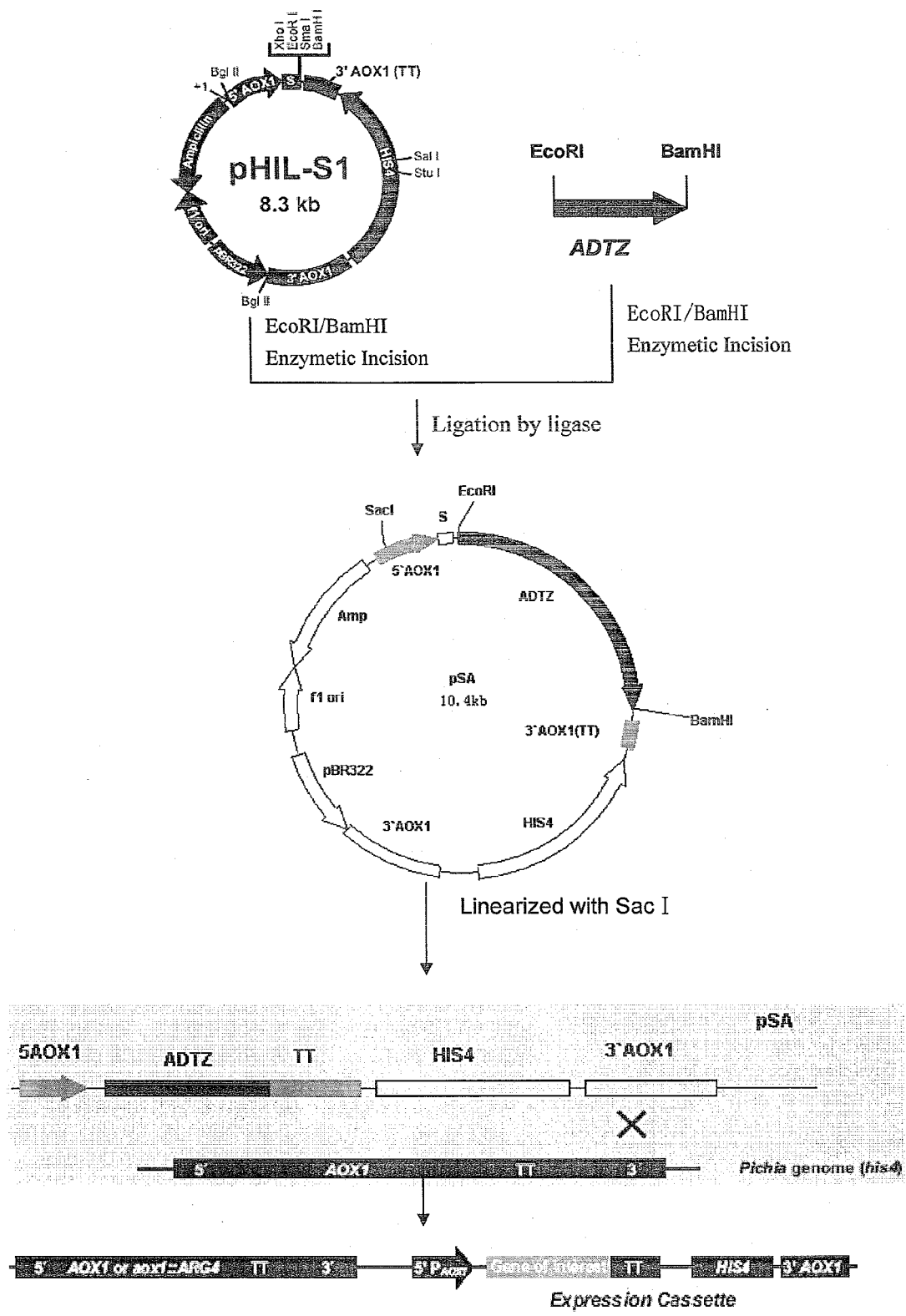

ADTZ' from example 7 was cloned to pHIL-S1 to construct expression vector pHIL-S1-ADTZ following standard procedure (Sambrook, et al. 1989, Molecular Cloning, Cold Spring Harbor Laboratory Press, United States). The product was analyzed by enzymatic incisions and sequenced. Detail as following:

As shown in FIG. 14, the construction of hybrid plasmid containing ADTZ gene was as following:

Plasmid pHIL-S1 and fragment ADTZ' were cleaved by EcoRI+BamI two enzyme incisions. The mixtures were subjected to 0.8% agarose electrophoresis, and extracted from the gel. Recombinant plasmid pHIL-S1-ADTZ was constructed from vector pHIL-S1 and ADTZ gene by T4 DNA ligase enzyme.

E. coli DH5α competent cells were prepared using $CaCl_2$ method and transformed. The transformed cells were selected, and plasmid DNA obtained from alkaline extraction. Recombinant plasmid DNA was purified by precipitation with PEG (Sambrook, et al. 1989, Molecular Cloning, Cold Spring Harbor Laboratory Press, United States). DNA sequence was determined on an ABI377 DNA sequencer using T7 and SP6 sequencing primers.

Figure 11:
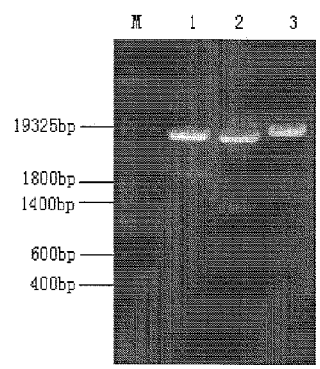

Enzyme incision of recombinant plasmid pHIL-S1-ADTZ (pSA) was shown in FIG. 11: BamHI and EcRI two enzyme incision (sample 1) showed a single band (~2000 bp), HindIII single enzyme incision (sample 2) showed three bands (~1400 bp, 600 bp and 500 bp), SacI single enzyme incision showed linear cleavage (indicating no SacI cleavage site in the inserted fragment).

EXAMPLE 9

Expression of Recombinant ADTZ Gene

Figure 12:
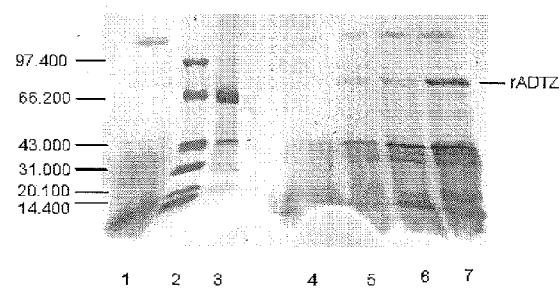
Figure 13:
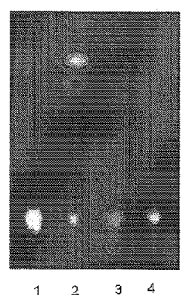

Recombinant plasmid pHIL-S1-ADTZ and expression vector pHIL-S1 were cleaved by SacI. The mixtures were subjected to 0.8% agarose electrophoresis. Linearized recombinant plasmid pHIL-S1-ADTZ and vector pHIL-S1 were extracted from the gel. $Mut^+$ transformants were selected following spheroplast transformation of Pichia pastoris GS115 (Pichia Expression kit manual, Invitrogen Inc. United States). Methanol was used as the only carbon source for the induced expression of Pichia pastoris GS115. SDS-PAGE of the incubation mixture showed clearly protein band following induced expression, while the control sample with no ADTZ gene showed no protein band. The results were shown in FIG. 12. Detail follows:

Homogeneous Recombination of Recombinant Plasmid in Pichia pastoris 9.1. Linearization of Plasmids Recombinant plasmid pHIL-S1-ADTZ (pSA) and expression vector pHIL-S1 were cleaved by SacI. The later was used as control for the following experiment.

pSA enzyme incision (120 μl): 12 ml Buffer L+8 ml SacI+ 100 ml pSA.

pHIL-S1 enzyme incision (120 μl): 12 ml Buffer L+8 ml SacI+100 ml pHIL-S1.

The mixtures were subjected to 0.8% agarose electrophoresis. Linearized recombinant plasmid pSA and vector pHIL-S1 were extracted from the gel.

9.2. Incubation of Pichia pastoris for Spheroplast Transformation 9.2.1. Inoculated 10 ml of YPD (Yeast Extract Peptone Dextrose medium) with a single colony of Pichia pastoris GS115. Grew overnight at 30° C. in a shaking incubator (250-300 rpm).

9.2.2. Inoculated 200 ml of YPD with 5, 10, and 20 μl of the overnight culture. These samples were incubated overnight at 30° C. in a shaking incubator (250-300 rpm).

9.2.3. The three cultures were tested for $OD_{600}$. The ones with $OD_{600}$=0.2-0.3 were selected, and pelleted by centrifugation at 1500×g for 5 min. The supernatant was discarded. The cells were used for spheroplast transformation.

9.3. Preparation of Pichia pastoris GS115 Spheroplasts 9.3.1. The cell pellet was re-suspended in 20 ml sterile water, and transferred to two 10 ml centrifuge tubes.

9.3.2. The cells were pelleted by centrifugation at 1500×g for 5 min. The supernatant was discarded.

9.3.3. The cell pellet was washed with fresh prepared SED, followed by centrifugation at 1500×g for 5 min. The supernatant was discarded.

9.3.4. The cell pellet was washed with 1M Sorbitol solution, followed by centrifugation at 1500×g for 5 min. The supernatant was discarded.

9.3.5. The cell pellet was re-suspended in 10 ml SCE.

9.3.6. Zymolyase in a tube was thawed and mixed by flicking the tube.

9.3.7. 7.5 μl of Zymolyase was added and incubated for 30 min at 30° C.

9.3.8. The cells were pelleted by: centrifugation at 1500×g for 5 min. The supernatant was discarded.

9.3.9. The transformation mixture was washed with 1M Sorbitol solution, mixed by flicking the tube to disperse the precipitate. The cells were pelleted by centrifugation at 750×g for 5 min at room temperature. The supernatant was discarded.

9.3.10. The cell pellet was washed with 10 ml CaS solution, followed by centrifugation at 750×g for 5 min. The supernatant was discarded.

9.3.11. The cell pellet was re-suspended in 0.6 ml CaS solution. The spheroplasts must be used within 30 min.

9.4. Spheroplast Transformation of Pichia pastoris GS115

9.4.1. Aliquots of 100 μl each of Pichia pastoris GS115 spheroplasts were transferred to three sterile centrifuge tubes A, B and C.

9.4.2. Tube A (no DNA) negative control, tube B (added 30 μl linearized vector pHIL-S1), tube C (added 30 μl linearized recombinant plasmid pSA, incubated for 10 min at room temperature). 3 ml of PEG/CaT was prepared at the same time.

9.4.3. Aliquots of 1 ml each of PEG/CaT were added to tube A, B and C, mixed gently and incubated for 10 min at room temperature.

9.4.4. The cells were pelleted by centrifugation at 750×g for 5 min. The supernatant was discarded.

9.4.5. The cell pellets were re-suspended in 150 μl SOS, incubated for 20 min at room temperature.

9.4.6. Aliquots of 850 μl 1M Sorbitol solution each were added to the tubes.

9.4.7. The entire transformations were plated on RD solid incubation plates using a sterile spreader (200 μl/plate). The plates were incubated at 28-30° C. Transformants appeared between 4-6 days.

9.5. Selection of Mut+ Transformants 9.5.1. Using a sterile toothpick, His+ transformants were patched on both MM and MD plates, the strains GS115/His+ Mut$^s$ Albumin and GS115/His+ Mut+ β-gal were also patched on the plates as controls.

9.5.2. Plates were incubated at 28-30° C. for 2 days.

9.5.3. After two days, scored the plates. Mut+ strains will grow normally on both plates, while Mut$^s$ will grow normally only on the MD plate but little or no growth on MM plate.

9.6. Induced Expression of the Recombinant Strains 9.6.1. Inoculated a single colony of His+Mut+ transformant in 25 ml BMG in a 250 ml baffled flask. Grew at 28-30° C. in a shaking incubator (250-300 rpm) until the culture reached $OD_{600}$=2-6 (~16-18 h).

9.6.2. Cells were harvested by centrifugation at 1500-3000×g for 5 min at room temperature. Supernatant was decanted and cell pellet was re-suspended in BMM to an $OD_{600}$ of 1.0 (100-200 ml BMM). The culture was placed in a 1-litter baffled flask and returned to incubator to continue growth at 250-300 rpm at 28-30° C.

9.6.3. 100% methanol was added to a final concentration of 0.5% to maintain induced expression.

9.6.4. After 96 h, the expression culture was centrifuged for 2-3 min, supernatant was transferred to a separate tube and stored at −80° C. for purification of expression product.

The supernatant of the culture after 96 h induction was analyzed. Total amount of protein was 0.23 mg/ml. The molecular weight of the protein product is consistent with the predicted value of 76.95 kDa by BioEdit.

EXAMPLE 10

Purification of Recombinant ADTZ

The recombinant expression culture was precipitated with 70% saturation $(NH_4)_2SO_4$, producing crude enzyme as precipitate. The crude enzyme was dissolved in equal volume of PBS, centrifuged. The supernatant was loaded on a hydrophobic Phenyl Sepharose column; active product was collected from gradient elution. The product was subjected to dialysis desalination and concentrated after equilibration with PBS. The concentrated crude enzyme solution was then purified by metal chelating affinity chromatography using Chelating Sepharose column. The active peak was eluted using pH gradient pH 7.5-6.0 and fraction collected. Details follow:

10.1. Crude Enzyme from $(NH_4)_2SO_4$ Precipitation $(NH_4)_2SO_4$ powder was added to the recombinant expression culture until 40% saturation followed by centrifugation at 10000 g for 20 min at 4° C. The supernatant was added more $(NH_4)_2SO_4$ until 70% saturation. Crude enzyme was obtained from centrifugation at 10000 g for 20 min at 4° C.

10.2. Hydrophobic Interaction Chromatography

ADTZ crude enzyme was dissolved in equal volume of 0.02 M PBS (pH 6.0). and centrifuged at 4000 g for 10 min at 4° C. Supernatant was loaded on a Phenyl Sepharose column (Pharmacia Biotech. Inc., United States) which had been washed to background using 0.02M PBS+30% saturation $(NH_4)_2SO_4$, pH 6.0. Gradient elution with A (0.02M PBS+10% saturation $(NH_4)_2SO_4$, pH 6.0) and B (0.02 M PBS, pH 6.0) gave an active product. The product was subjected to dialysis desalination and concentrated after equilibration with F solution (0.02 M PBS+5 M NaCl, pH 7.5) to 1 mg/ml.

10.3. Metal Chelating Affinity Chromatography

Chelating Sepharose (Pharmacia Biotech. Inc., United States) was saturated with 0.2 M $CuCl_2$, and then equilibrated with water and F solution (0.02 M PBS+5 M NaCl, pH 7.5). The pooled fractions from hydrophobic interaction chromatography were loaded and purified with non-linear pH gradient using buffer G (0.02 M PBS+0.5 M NaCl, pH 7.5-6.0, non-linear gradient incremented by 0.5 pH unit). The product peak was collected, and analyzed using SDS-PAGE.

Conclusion: 58 mg purified recombinant ADTZ was obtained from 1 liter expression culture, purity was greater than 95%.

EXAMPLE 11

Test of Recombinant ADTZ Activity

Recombinant ADTZ activity was test following protocols in example 2.1. Test mixtures: (1) Enzyme mixture: 1 μl $AFB_1$ solution (0.5 μg/μl in MeOH, evaporated under nitrogen)+recombinant ADTZ enzyme solution (0.1 mg/ml, 300 μl)+0.5 μl MgSO4+10 μl PEG200; (2) Deactivated enzyme mixture: 1 μl $AFB_1$ solution (0.5 μg/μl in MeOH, evaporated under nitrogen)+deactivated recombinant ADTZ enzyme solution (0.1 mg/ml, 300 μl, preheated at 100° C. for 5 min)+0.5 μl MgSO4+10 μl PEG200; (3) control mixture: 1 μl $AFB_1$ solution (0.5 μg/μl in MeOH, evaporated under nitrogen)+300 μl PBS buffer+0.5 μl MgSO4+10 μl PEG200. The test mixtures were mixed thoroughly, reacted for 1 h at 30° C., $AFB_1$ (0.5 μl×2) was added every hour (total AFB1: 2 μg). After the addition, the reactions continued for 6 more hours. After the reaction, TLC (as described in example 1) showed new product with Rf~1 (=0.93) for recombinant ADTZ, very similar to natural ADTZ, indicting activity of recombinant ADTZ in transforming $AFB_1$. Result was shown in FIG. 13.

EXAMPLE 12

Bioactivity of Recombinant ADTZ in Detoxifying $AFB_1$

The bioactivity of recombinant ADTZ was tested following protocols in example 2.2, where recombinant ADTZ was used instead of natural ADTZ. The number of mutant colonies of active recombinant ADTZ test sample is very similar to the negative control (DMSO control sample) (MR<2). The mutant colonies number of the buffer control sample and deactivated recombinant ADTZ test sample are significantly higher than that of the negative control sample (MR>2), and are very close to the positive control ($AFB_1$ control sample). These results demonstrate the bioactivity of recombinant ADTZ. The results are shown in the following table.

| Sample | Number of mutant colonies/plate | MR | Inhibition (%) |
|---|---|---|---|
| PBS-control sample | 379 ± 57 | 12.03 | ~ |
| Deactivation recombinant enzyme test sample | 353 ± 63 | 11.66 | ~ |
| Recombinant enzyme test sample | 30 ± 01 | 1.01 | 98.06 |
| $AFB_1$ control sample | 383 ± 65 | 12.35 | ~ |
| DMSO control sample | 26 ± 8 | ~ | ~ |

We claim:

1. An isolated detoxifizyme with activity of transforming aflatoxin $AFB_1$, said transformation resulting in detoxification of said aflatoxin, wherein said detoxifizyme isoelectric point is 5.3-6.8 and molecular weight is 73-77 kilodaltons and comprising the amino acid sequence of SEQ ID NO: 1.

2. An isolated gene comprising a nucleic acid sequence coding for the detoxifizyme as claimed in claim 1.

3. The isolated gene of claim 2, wherein said gene contains the nucleic acid sequence of SEQ ID NO: 2.

4. A recombinant expression vector comprising the gene as claimed in claim 3.

5. An isolated transformed host cell transformed with the recombinant expression vector as claimed in claim 4.

6. A method for preparation of a detoxifizyme as claimed in claim 1 said method comprising: cultivating the transformed host cell as claimed in claim 5; and separating, purifying and recovering the expressed detoxifizyme.

7. A method for detoxifying feed or food, comprising: providing the detoxifizyme as claimed in claim 1; and applying the detoxifizyme as a detoxification additive for detoxifying feed or food.

* * * * *